United States Patent [19]

Burnouf et al.

[11] Patent Number: 5,252,709
[45] Date of Patent: Oct. 12, 1993

[54] CHROMATOGRAPHIC SEPARATION OF PLASMA PROTEINS

[75] Inventors: Thierry Burnouf; Miryana Burnouf-Radosevich, both of Wavrin, France

[73] Assignee: Centre Regional de Transfusion Sanguine de Lille, Lille, France

[21] Appl. No.: 460,972

[22] PCT Filed: Feb. 8, 1989

[86] PCT No.: PCT/FR89/00050
§ 371 Date: Apr. 6, 1990
§ 102(e) Date: Apr. 6, 1990

[87] PCT Pub. No.: WO89/12065
PCT Pub. Date: Dec. 14, 1989

[30] Foreign Application Priority Data

Jun. 7, 1988 [FR] France .................. 88 07530

[51] Int. Cl.$^5$ .................. C07K 3/22; C07K 15/06
[52] U.S. Cl. .................. 530/382; 530/381; 530/383; 530/395; 530/416
[58] Field of Search .............. 530/381, 382, 383, 387, 530/392, 394, 416, 395

[56] References Cited

U.S. PATENT DOCUMENTS

| | | | |
|---|---|---|---|
| 4,278,594 | 7/1981 | Amrani | 530/383 |
| 4,341,764 | 7/1982 | Wallace et al. | 530/383 |
| 4,578,218 | 3/1986 | Saundry et al. | 530/383 |
| 4,670,543 | 6/1986 | Bourgois et al. | 514/2 |
| 4,764,369 | 8/1988 | Neurath et al. | 424/89 |
| 4,822,681 | 4/1989 | Schössler et al. | 428/405 |
| 4,883,598 | 11/1990 | Riethorst et al. | 530/381 |
| 5,021,243 | 6/1991 | Becher et al. | 424/530 |
| 5,043,429 | 8/1991 | Zimmerman et al. | 530/383 |
| 5,097,018 | 3/1992 | Rubinstein | 530/381 |
| 5,110,907 | 5/1992 | Kosow et al. | 530/381 |

FOREIGN PATENT DOCUMENTS 0176926 9/1985 European Pat. Off. .
8604486 8/1986 PCT Int'l Appl. .

OTHER PUBLICATIONS

Kato et al., J. Aromatog., vol. 245, pp. 193-211, (1982).
Kazama et al., Haemostasis, vol. 5, pp. 329-340 (1976).
Scopes, Protein Purification-Principles and Practice, 2nd Ed., (Springer-Verlag, New York) pp. 112-113 (1988).
Fractogel TSK, Polymeric Media for Biochromatography.
Clarke et al., (1977) Experimental Biochemistry, 2nd Edition, W. H. Freeman and Company, pp. 18-19.

*Primary Examiner*—Jeffrey E. Russel
*Attorney, Agent, or Firm*—Birch, Stewart, Kolasch & Birch

[57] ABSTRACT

The invention relates to a process for separating proteins from a fraction of human or animal plasma.

According to this process, a solubilized fraction of cryoprecipitated plasma is subjected to a single stage of chromatography on a moderately ionic anion exchange resin permitting hydrophobic interactions to take place, which does not adsorb certain proteins and fixes others, which are then eluted by increasing the ionic strength of the buffer by the addition of NaCl.

The process according to the invention makes it possible, in particular, to obtain a Factor VIII concentrate of high purity that can be used for the treatment of haemophilia A. The process also makes it possible to obtain concentrates of fibrinogen, Von Willebrand's factor and fibronectin.

15 Claims, No Drawings

CHROMATOGRAPHIC SEPARATION OF PLASMA PROTEINS

The present invention relates to the separation of proteins of a fraction of human or animal plasma by anion-exchange chromatography using a technique that makes it possible to obtain, in a single stage, a very high purification rate, in particular for Factor VIII, for fibrinogen and for Von Willebrand's factor.

The provision of blood proteins for therapeutic purposes necessitates the use of purification techniques that make it possible to obtain products of high purity and completely free of contaminants, particularly other proteins or substances of foreign origin such as antibodies.

It is essential, for instance, in treating haemophilia A, to have at one's disposal Factor VIII concentrates of very high purity; indeed, the patients are given numerous, repeated injections of Factor VIII concentrates and, at the same time, substantial quantities of fibrinogen and immunoglobulins which can induce undesirable immune responses. Hence, repeated injections of insufficiently purified Factor VIII can be carried out only with plasma concentrates of the same group in order to avoid typical transfusion accidents due to differences in blood group and caused by the presence of immunoglobulins.

Factor VIII concentrates are most often prepared from a fraction of cryoprecipitated human plasma. The purity of Factor VIII concentrates, generally obtained from industrial scale human plasma processing centers, is often in the order of 1 IU/mg and does not generally exceed the limits of 10 to 20 IU/mg. Conventional production techniques make use of precipitation stages that aim to eliminate, often very inadequately, protein contaminants such as fibrinogen, fibronectin and immunoglobulins. These techniques can use or combine precipitation at low temperature (10° C.), or the addition of protein precipitating agents; hydrophilic polymers such as PEG (Newman et al., Br. J. Haematol 21:1-20, 1971; Hao et al., in Methods of Plasma Protein Fractionation, Academic Press 1980, PP. 57-74), polyvinylpyrrolidone (Casillas and Simonetti, Br. J. Haemato, 50:665-672, 1982), dextran, Ficoll, Percoll, hydroxyethylated starch and albumin have thus been proposed as Factor VIII precipitating agents (Farrugia et al., Thromb Haemostas, 51:338-342, 1984). The same applies to the use of glycine and sodium chloride recommended by Thorell and Blömback. Similarly, some authors (Ng et al., Thrombosis Res., 42:825-834, 1986) have succeeded in combining three precipitating agents, namely: PEG, glycine and sodium chloride, to obtain Factor VIII concentrates having a specific activity of between 10 and 16 IU/mg.

Use has also been made of steric exclusion chromatography, or gel filtration, techniques aimed at recovering a fraction of high molecular weight containing the Factor VIII:C—Von Willebrand's factor complex partially free of fibrinogen. This technique provides, at a low rate of output, a product the specific activity of which does not exceed 30 IU/mg and which necessitates the addition of albumin as a stabilizer (leading to a drop in specific activity to approximately 3 to 5 IU/mg). This technique poses a number of problems regarding adaptation to large scale production as it is difficult to maintain the resolving power of industrial gel filtration columns over a period of time.

Factor VIII concentrates have also been produced by incorporating in the production program contact with microballs of porous silicon dioxide designed to imprison protein contaminants of low molecular weight (Margolis et al., Vox Sang. 46:341-348, 1984). The specific activity of the product remains relatively small: 1 IU/mg.

New techniques have recently made their appearance in the preparation of very high purity Factor VIII concentrates. The firms of Hyland and Travenol, for instance, have proposed concentrates obtained using immune affinity chromatography methods (Zimmerman and Fulcher, Thrombosis Res., Suppl. VII, p. 58, 1987; Berntorp and Nilsson, Thrombosis Res., Suppl. VII, p.60, 1987; Levine et al., Thrombosis Res, Suppl. VII, 1987). These techniques consist in purifying Factor VTIII using anti-Factor VIII:C or anti-Von Willebrand's factor antibodies immobilized on a chromatographic medium. These techniques perform well but necessitate the use of drastic solutions to desorb Factor VIII either of its antibodies or of the Von Willebrand's factor. An additional ultrafiltration stage aimed at removing the undesirable chemical agents is thus required, but it can be prejudicial to the biological activity of Factor VIII. The specific activity of Factor VIII can reach 1000 IU/mg to 3000 IU/mg in the course of production, but its instability necessitates the addition of a stabilizer, such as albumin, before the freeze drying stage, which reduces the specific activity of Factor VIII to 3 to 5 IU/mg. The major drawback of purification by immune affinity is, nonetheless, the presence of residual antibodies; as these are of murine origin, they can lead to the occurrence in the patients of immune responses towards these proteins foreign to the human organism.

Ion-exchange chromatography techniques have also been used but, given the complexity of the operating procedures and the low yields achieved, these techniques have remained confined to the laboratory.

An article by J. J. Morgenthaler (Thromb. Haemostas., Stuttgart, 47 (2) 124-127 (1982)), for instance, discusses the purification of Factor VIII:C using a polyethylene glycol precipitate, by passage through a modified Sepharose resin. No indication is given on the yield or reproducibility of the different techniques tested.

It is thus absolutely essential to have at one's disposal new methods for obtaining protein concentrates, and in particular Factor VIII, that can be applied on an industrial scale and give very high purify products completely free of proteins of foreign origin such as antibodies of animal origin.

The Applicant has thus developed a purification process using anion-exchange chromatography which, thanks to the appropriate choice of the resin used, enables the proteins sought to be separated using a single chromatography column under conditions that are suitably designed to make it possible to dispense with subsequent processing, such as ultrafiltration, which increases the complexity of the process and reduces the activity of the purified protein.

The invention thus relates to a process for separating plasma proteins and, more particularly, Factor VIII, fibrinogen, fibronectin and Von Willebrand's factor, characterized in that a solubilized fraction of a cryoprecipitate of human plasma is subjected to chromatographic treatment on an anion exchange resin of a relatively moderate ionic nature and also permitting the occurrence of hydrophobic interactions, which does not adsorb certain proteins and which fixes others, which are then eluted specifically by increasing the ionic strength of the buffer.

The process is also applicable to a plasma of animal origin, for example, porcine, for special cases involving haemophilic patients with inhibiting serum who cannot be treated using Factor VIII of human origin.

One can thus use as a starting fraction a fraction of cryoprecipitated plasma which may have undergone a pre-purification treatment. This pre-treatment can consist, for example, of precipitation with alumina gel and/or precipitation at low temperature in accordance with the conventional techniques for treating such fractions.

When testing the different resins for chromatographic separation, it was observed that the most satisfactory results were obtained using DEAE groups fixed on a vinyl polymer gel, such as FRACTOGEL TSK, a semirigid gel which is a copolymer of oligoethyleneglycol, glycidylmethacrylate, and pentaerythroldimethacrylate. A resin of this type is commercially available under the name of FRACTOGEL TSK-DEAE 650 (M) (Merck), a semirigid, crosslinked gel matrix which consists of hydrophilic vinyl polymers modified by the addition of ion-exchanger groups on the internal and external surfaces. This chromatographic medium has given far better results than those obtained with the other gels tested, such as DEAE-Sepharose CL-6B, DEAE-Sepharose CL-6B Fast-Flow (Pharmacia), DEAE-Sepharose 4B or DEAE-Trisacryl LS (IBF).

The use of a gel similar to FRACTOGEL-TSK-DEAE (M) is described by Y. Kato et al. (J. Chromato; 245, 1982, 193-211) and recommended for the medium-performance, industrial scale chromatographic separation of very large size proteins. The retention-elution capacity of this gel is based on a low ion exchange capacity and large pore size.

The Applicant has thus shown that this type of gel made it possible to adsorb preferentially the very large size complexes that form between Factor VIII and Von Willebrand's factor. Moreover, through the choice of loading and elution buffers, the Applicant has exploited the slightly hydrophobic bonds that form owing to the prolonged retention of the large-sized complexes on the polyvinyl medium. This advantage offered by the gel had not been highlighted previously.

By using such a resin to treat a fraction of plasma containing Factor VIII, for example a pre-purified solution of the cryoprecipitate, we obtain, under appropriate buffer conditions, a Factor VIII concentrate of very high purity and the quality of which can be assimilated to that of a plasma concentrate of a single group, at a concentration in the order of 50 IU/ml (specific activity higher than 100 IU/mg), without there being any need for an ultrafiltration stage, and one of high stability, that is to say not necessitating the addition of a protein type stabilizer. With the same chromatography, it is also possible to obtain fibrinogen, fibronectin and Von Willebrand's factor enriched fractions conforming to the physical chemistry parameters that satisfy requirements for therapeutic purposes or for use as a reagent. Moreover, the fibrinogen can be further concentrated for use as a biological glue, in accordance with European patent application No. 88 401961.3.

The process according to the present invention is implemented as follows. The plasma fraction prepurified and containing the major proteins of the cryoprecipitate, i.e. fibrinogen, Factor VIII, fibronectin and Von Willebrand's factor, passes over an anion exchange resin such as the one specified hereabove; the Factor VIII, the Von Willebrand's factor (all or a substantial part, depending on the quantity of initial material) and the fibronectin are adsorbed on the resin, while the fibrinogen is found in the filtrate of the non-adsorbed proteins.

By a first increase in the ionic strength the buffer, the fibronectin and a substantial part of the Von Willebrand's factor are eluted.

By an additional increase in the ionic strength of the buffer, the Factor VIII is eluted in the presence of small quantities of Von Willebrand's factor and can be freeze dried directly, without there being any need to add a stabilizer thereto or to subject it to an ultrafiltration stage.

The buffer used advantageously contains lysine in a proportion of approximately 2 to 4 g/l, as well as glycine in a proportion of approximately 8 to 11 g/l. The use of other amino acids, or even the use of only one of these two amino acids, gives far less satisfactory results.

The ionic strength of the buffer is increased, by adding sodium chloride. Indeed the use of this single resin, moderately ionic, and slightly hydrophobic, makes it possible to use this salt to desorb the Von Willebrand's factor before Factor VIII is eluted, thus making it unnecessary to use calcium chloride, which would then have to be removed by ultrafiltration, to dissociate Factor VIII and Von Willebrand's factor.

A virus inactivating treatment can, of course, be performed using a known technique at any stage in the process. In the event of a chemical virus inactivating agent being used, it will be appropriate to carry out this inactivation just before the passage of the plasma fraction over the resin. In this way, the chromatographic stage will serve to efficiently eliminate the inactivating agents.

Good results have been obtained using the solvent-detergent inactivating technique, as described in European patent application No. 0 131 740.

To prepare Factor VIII, the chromatography stage can be carried out on any protein fraction containing it, for example on a prepurified cryoprecipitated plasma fraction that has been subjected to a treatment with alumina gel, possibly followed by precipitation at low temperature, in accordance with the conventional methods for producing Factor VIII concentrates, as described in European patent application 86 104297 6.

The specific activity of Factor VIII:C in the initial fraction can be as low as 0.1 IU/mg. The purification factor obtained by a single anion exchange chromatography stage, according to the invention, is in the order of 400 to 700 fold. The yield of this stage is between 75 and 90%.

The Factor VIII concentrate obtained is of very high purity, its specific activity being greater than 100 IU/mg of proteins. It is free of fibrinogen and immunoglobulins G, and it is considerably depleted of fibronectin. This product is free of human blood group antibodies, or only contains them in very small proportions and it can thus be likened to a concentrate of single group quality in accordance with the standards recommended by the European Pharmacopoeia, even when using as an initial material a plasma not selected according to blood group. It can thus be used to great advantage in therapeutics and quite especially in the treatment of haemophilia A, which necessitates repeated routine injections. It can also be used as a reagent in any test or analysis necessitating a Factor VIII of very high purity.

The other fractions separated by this chromatography column are also of interest on account of the proteins that they contain, namely, on one hand, fibrinogen, which is recovered in the first filtrate, and, on the other hand, fibronectin and Von Willebrand's factor, which are eluted by the first increase in the ionic strength of the buffer.

The following examples illustrate the invention, without thereby limiting its scope.

EXAMPLE 1

A) Pre-purification and Virus Inactivation

As a starting material, use is made of a cryoprecipitate of human plasma resuspended in an aqueous solution of sodic heparin (at 2 U/ml) and containing Factor VIII with a specific activity of between 0.6 and 1.1 IU/mg.

The pH of the suspension is adjusted to 7-7.1 with 0.1M acetic acid.

This suspension of cryoprecipitate is subjected to purification by treatment with alumina gel and cold precipitation. Aluminum hydroxide is added to the suspension (108 g of 2% Al(OH)$_3$ for 1 kg of cryoprecipitate) with stirring for 5 minutes at ambient temperature. The pH is adjusted to 6.5-6.6 with 0.1M acetic acid, and the suspension is then cooled to 14°-16° C., with stirring. As soon as the desired temperature has been reached, centrifuging is carried out at 14°-16° C., the supernatant is harvested and it is sterilized by filtration.

This prepurified solution is subjected to a virus inactivation treatment using solvent-detergent, in the presence of Tween-TNBP, in accordance with the method described in European patent application No. 0 131 740.

B) Chromatographic Separation on FRACTOGEL TSK-DEAE

A chromatography column is prepared with FRACTOGEL TSK-DEAE 650 (M) (Merck) resin. 0.5L of FRACTOGEL is provided per kg of cryoprecipitate. The column is washed with 5 volumes of 0.1M NaCl solution, and then balanced with a buffer containing:

trisodic citrate (2.94 g/l), calcium chloride (1 mN), sodium chloride (0.11M), glycine (9 g/l) and lysine (3 g/l).

The pre-purified cryoprecipitate solution described in A) is injected into the column.

The following filtrate and eluates are collected and their protein content is monitored by measuring absorption at 280 nm (hereinafter designated by O.D).

The first filtrate shows a peak of proteins not adsorbed by the column corresponding essentially to fibrinogen (see example 3).

After this peak has been passed, when the O.D. has dropped back to the base line, the column is eluted with the same buffer the ionic strength of which is increased a first time by adding NaCl, at a final concentration of 0.15M. This buffer desorbs a protein peak containing the bulk of the Von Willebrand's factor and the fibronectin (see example 4).

After this peak has been passed, when the O.D. has dropped back to the base line, the ionic strength of the buffer is increased a second time by adding NaCl at a final concentration cf 0.25M.

Under these conditions, the Factor VIII is eluted at a concentration in the order of 30 to 40 IU/ml.

EXAMPLE 2

Preparation of the Factor VIII Concentrate

The Factor VIII solution obtained using the chromatographic process described in example 1 is sufficiently pure and concentrated to be placed directly in bottles and freeze dried, without any additional ultrafiltration stage.

The concentration can be adjusted if necessary by diluting with the same elution buffer for adjusting specific activity per bottle in accordance with the legal standards in force.

The mean composition of the solutions obtained is as follows:

| Proteins (g/l) | 0.16-0.25 |
|---|---|
| Factor VIII:C (IU/ml) | 30-45 |
| Specific activity of | 120-250 |
| Factor VIII:C (IU/mg) | <0.1 |
| Fibrinogen (g/l) | |
| Von Willebrand's factor: Ag (U/ml) | 11-23 |
| Von Willebrand's factor: RCO (U/ml) | 10-20 |
| Factor VIII: Ag (U/ml) | 35-60 |
| IgG (mg/ml) (nephelometry) | <0.011 |
| Natural and immune anti-A-antibodies | 0-2 |
| Fibronectin (mg/l) | 15-40 |

After freeze drying, the product is clear and instantaneously soluble. The amount of Factor VIII:C is stable over 24 hours at ambient temperature.

Injections in man indicate Factor VIII:C recovery comparable with that obtained with less pure products. Similarly, half-life is equivalent to that of the other products.

This concentrate proves to be a product of high therapeutic value, particularly suitable for the repeated injections that are required in the treatment of haemophilia A.

EXAMPLE 3

Purification of a Fibrinogen Concentrate

The first filtrate of chromatography on DEAE-FRACTOGEL described in example 1 chiefly contains fibrinogen, but also albumin, immunoglobulins and virus inactivating agents (Tween and TNBP).

The fibrinogen is purified from this solution by a further chromatography stage on a heparin-sepharose resin column.

This chromatography stage is carried out in the same buffer as the preceding one, adjusted to 0.06M NaCl, thus making it possible to prevent dialysis between the two chromatography stages.

The filtrate from the first chromatography stage is diluted to obtain an osmolarity of 280 mOsm at a pH of 6.5 before being injected onto the second column. The second filtrate is found to contain albumin, immunoglobulins, Tween and TNBP. The fibrinogen is adsorbed on the column.

When the O.D of the filtrate has dropped back to the base level, the column is eluted with the same buffer after its ionic strength, has been increased by the addition of NaCl at a final concentration of 0.16M.

The fraction of fibrinogen collected is then concentrated and dialyzed on a cassette system. The concentrated product is placed in bottles and freeze dried.

This concentrated fibrinogen meets the quality standards laid down by the European Pharmacopoeia.

Furthermore, it can serve as a substrate for the preparation of biological glue in accordance with European patent application No. 88 401961.3.

EXAMPLE 4

Preparation of the Von Willebrand's Factor Concentrate

The eluted fraction obtained from chromatography using DEAE-FRACTOGEL in the presence of 0.15M of NaCl, described in example 1, is considerably enriched with Von Willebrand's factor and fibronectin. It still contains some Tween and TNBP.

This fraction is diluted to bring its osmolarity to 385–390 mOsm with the chromatography basic buffer (trisodic citrate, calcium chloride, lysine, glycine, pH 7, osmolarity 18 mOsm).

It is then injected onto a second column of DEAE-FRACTOGEL, with the same buffer as before and containing NaCl at a final concentration of 0.11M, adjusted to a pH of 7 and 387 mOsm.

Under these conditions, the Tween and TNBP can be removed very efficiently.

As the initial solution already contains a very high concentration of Von Willebrand's factor, the latter is fixed on the column to a far greater degree than during passage through the first column. The fixing capacity of the column is at least 160 U Ag/ml (antigen unit of Von Willebrand's factor) or 100 RCO/ml (ristocetin cofactor units).

The fraction containing the Von Willebrand's factor is eluted by the addition of NaCl at a final concentration of 0.15M to the buffer.

The eluted Von Willebrand's factor is sufficiently concentrated not to necessitate additional ultrafiltration; it is placed in bottles and freeze dried.

The concentrate obtained is of very high purity and has a specific activity in excess of 100 U RCO/mg. It still contains some fibronectin, but this is not prejudicial to its activity.

EXAMPLE 5

Preparation of a Fibronectin Concentrate

A fibronectin concentrate can also be prepared from the same initial eluate as in example 4.

The Von Willebrand's factor and the fibronectin can, in fact, be separated on the basis of their difference in molecular weight. Using gel filtration on a column of Sephacryl S-400 (R) (Pharmacia), for example, a first fraction of high molecular weight containing the Von Willebrand's factor is separated, followed by a fraction containing the fibronectin, which can be directly bottled and freeze dried.

We claim:

1. A process for the separation and concentration of Factor VIII, von Willebrand's factor, fibronectin and fibrinogen from plasma containing Factor VIII, von Willebrand's factor, fibronectin and fibrinogen which comprises:
   a) chromatographing with a buffer a solubilized fraction of cryoprecipitated plasma on an exchange resin having DEAE groups fixed on a vinyl polymer-type gel which adsorbs Factor VIII, von Willebrand's factor, and fibronectin, and which allows fibrinogen to pass into a first eluate wherein said exchange resin is a Fractogel TSK;
   b) increasing the ionic strength of said buffer which allows said fibronectin and said von Willebrand's factor to pass into a second elutate; and further
   c) increasing the ionic strength of said buffer which allows said Factor VIII to pass into a third eluate.

2. A process for the separation and concentration of Factor VIII, von Willebrand's factor, fibronectin and fibrinogen from plasma containing Factor VIII, von Willebrand's factor, fibronectin and fibrinogen which comprises:
   a) chromatographing with a buffer a solubilized fraction of cryoprecipitated plasma on an exchange resin having DEAE groups fixed on a vinyl polymer gel which adsorbs Factor VIII, von Willebrand's factor, and fibronectin, and which allows fibrinogen to pass into a first eluate;
   b) increasing the ionic strength of said buffer which allows said fibronectin and said von Willebrand's factor to pass into a second eluate; and further
   c) increasing the ionic strength of said buffer which allows said Factor VIII to pass into a third eluate.

3. The process according to claim 1, wherein the specific activity of Factor VIII:C in the initial fraction is greater than or equal to 0.1 IU/mg.

4. The process according to any one of claims 1 or 3, wherein the initial fraction has undergone a pre-purification treatment, comprising:
   treating with aluminium hydroxide;
   cooling to 14°–16° C.; and
   centrifuging and harvesting the supernatant.

5. The process according to claim 1, wherein said buffer contains lysine and glycine.

6. The process according to claim 5, wherein said buffer contains 2 to 4 g/l of lysine and 8 to 11 g/l of glycine.

7. The process according to claim 1, wherein said ionic strength of said buffer is increased using sodium chloride.

8. The process according to claim 7, wherein the sodium chloride concentration is 0.11M in the case of stage a), 0.15M in that of stage b), and 0.25M in that of stage c).

9. The process according to claim 1, wherein a virus inactivating treatment is carried out in the presence of solvent-detergent inactivating agents on the plasma fraction just before subjecting it to said chromatographic separation stage (a).

10. The process according to claim 1, wherein said exchange resin is Fractogel TSK-DEAE 650 (M).

11. The process according to claim 1, wherein said plasma cryoprecipitate has undergone a pre-purification treatment.

12. The process according to claim 11, wherein said pre-purification treatment consists of (a) precipitation with alumina gel and precipitation at low temperature or (b) precipitation at low temperature.

13. The process of claim 1, further comprising purifying said first eluate by chromatography on heparin-sepharose resin to produce a fibrinogen concentrate.

14. The process of claim 1, further comprising purifying said second eluate by chromatography on the same resin as in stage (a), and eluting by use of the same buffer as used therein, adjusted to 0.15M NaCl, to produce a concentrate of Von Willebrands's factor.

15. The process of claim 1, further comprising purifying the eluate of stage b) by an additional stage of gel filtration to produce a fibronectin concentrate.

* * * * *